United States Patent
Lawrence et al.

(10) Patent No.: US 6,895,970 B1
(45) Date of Patent: May 24, 2005

(54) CUSTOM TRAY FOR REDUCING DENTAL CLENCHING

(76) Inventors: Eric S. Lawrence, c/o 45 E. Juniper La., Moreland Hills, OH (US) 44022; Harvey N. Silverman, c/o 2605 Butternut La., Pepper Pike, OH (US) 44122; Robert Berghash, c/o 73 Oakgrove Dr., Williamsville, NY (US) 14221

( * ) Notice: Subject to any disclaimer, the term of this patent is extended or adjusted under 35 U.S.C. 154(b) by 445 days.

(21) Appl. No.: 10/011,252

(22) Filed: Dec. 6, 2001

(51) Int. Cl.[7] ................................................ A61F 5/56
(52) U.S. Cl. ........................ 128/848; 128/859; 128/861; 602/902
(58) Field of Search ................................ 128/846, 848, 128/859–862; 433/6; 602/902

(56) References Cited

U.S. PATENT DOCUMENTS

| | | | |
|---|---|---|---|
| 4,568,280 A | | 2/1986 | Ahlin |
| 4,773,853 A | | 9/1988 | Kussick |
| 4,955,393 A | | 9/1990 | Adell |
| 5,003,994 A | | 4/1991 | Cook |
| 5,092,346 A | * | 3/1992 | Hays et al. ................ 128/848 |
| 5,117,816 A | | 6/1992 | Shapiro et al. |
| 5,165,424 A | | 11/1992 | Silverman |
| 5,277,202 A | | 1/1994 | Hays |
| 5,313,960 A | * | 5/1994 | Tomasi ..................... 128/848 |
| 5,316,020 A | | 5/1994 | Truffer |
| 5,427,117 A | | 6/1995 | Thornton |
| 5,462,066 A | | 10/1995 | Snyder |
| 5,513,656 A | | 5/1996 | Boyd, Sr. |
| 5,566,684 A | | 10/1996 | Wagner |
| 5,611,355 A | * | 3/1997 | Hilsen ....................... 128/848 |
| 5,624,257 A | | 4/1997 | Farrell |
| 5,645,420 A | | 7/1997 | Bergersen |
| 5,794,627 A | | 8/1998 | Frantz et al. |
| 5,795,150 A | | 8/1998 | Boyd |
| 5,823,193 A | | 10/1998 | Singer et al. |
| 5,829,441 A | | 11/1998 | Kidd et al. |
| 5,868,138 A | * | 2/1999 | Halstrom .................... 128/848 |
| 5,921,240 A | | 7/1999 | Gall |
| 6,041,784 A | | 3/2000 | Halstrom |
| 6,129,084 A | | 10/2000 | Bergersen |
| 6,170,485 B1 | | 1/2001 | Orrico |
| 6,280,196 B1 | | 8/2001 | Berghash |

FOREIGN PATENT DOCUMENTS

EP 0312368 12/1993

* cited by examiner

*Primary Examiner*—Michael Anthony Brown
(74) *Attorney, Agent, or Firm*—Thompson Hine LLP

(57) ABSTRACT

An orthotic device for reducing dental clenching is provided along with a method for custom fitting said device. The orthotic device includes a tray for receiving the user's upper teeth, a guide ramp for position the user's lower jaw, and a plurality of spacers for providing a gap between the tray and the user's lower posterior teeth during fitting of the orthotic device. When worn by the user, the orthotic device positions the user's upper and lower anterior teeth in substantial vertical alignment thereby preventing contact between a user's upper and lower posterior teeth.

19 Claims, 2 Drawing Sheets

CUSTOM TRAY FOR REDUCING DENTAL CLENCHING

TECHNICAL FIELD

The present invention relates generally to an orthotic device, and more particularly, to an orthotic device for reducing dental clenching by preventing contact between a user's upper and lower posterior teeth.

BACKGROUND OF THE INVENTION

Dental clenching is caused by the inappropriate isometric contraction of the temporalis muscles, which are used to elevate or close the lower jaw. Specifically, dental clenching occurs when the temporalis muscles further contract after the lower jaw is fully closed. The lower jaw is fully closed when the upper and lower posterior teeth contact one another. Accordingly, dental clenching refers to the static clenching of the posterior teeth by the temporalis muscles.

Chronic clenching of the posterior teeth, which occurs most often during sleep, can cause a multitude of problems including headaches and temporomandibular disorder ("TMD"). Therefore, dental clenching is commonly treated with intraoral devices that position a user's jaw to eliminate contact between the upper and lower posterior teeth. Because known intraoral devices must be professionally fitted and installed by a dentist, the treatment of dental clenching is frequently too expensive for those who suffer from the disorder. Additionally, conventional orthotics used by the majority of dental practitioners to treat TMD place hard acrylic between the posterior teeth for the patient to occlude on. The dental clencher, due to the fact that the posterior teeth are in contact with the acrylic will continue to clench on the orthotic and maintain the same symptoms.

In light of the foregoing, an improved orthotic device for reducing dental clenching which can be custom fit and installed by a user at a relatively low cost is desired.

SUMMARY OF THE INVENTION

In a first aspect of the present invention, an orthotic device for reducing dental clenching is provided including a generally U-shaped tray for receiving a user's upper teeth, the tray having an anterior region and two posterior regions. Each posterior region of the tray includes a bottom surface, the bottom surface having a spacer releasably attached thereto for providing a gap between the bottom surface and the user's lower posterior teeth during fitting of the orthotic device. In addition, the orthotic device includes a ramp portion attached to the tray, the ramp portion including a guide ramp extending downwardly and posteriorly from the anterior region of the tray for engaging at least one of the user's lower anterior teeth. By engaging the guide ramp with at least one of the user's lower anterior teeth, the user's lower jaw is advanced to bring the user's lower anterior teeth into substantial vertical alignment with the user's upper anterior teeth. When the user's upper and lower anterior teeth are in substantial vertical alignment, the user's upper and lower posterior teeth cannot contact one another, thereby preventing dental clenching.

In a second aspect of the present invention, a method of custom fitting an orthotic device for reducing dental clenching is provided. The steps of the disclosed method include heating the orthotic device to a temperature at which it becomes moldable, inserting the orthotic device into a user's mouth such that the user's upper teeth are received in the orthotic device and such that a guide ramp of the orthotic device is directed downwardly and posteriorly into the user's mouth, posturing the user's lower jaw forward and bringing the user's lower anterior teeth into substantial vertical alignment with the user's upper anterior teeth, pushing the moldable guide ramp forward against the lingual side of the user's lower anterior teeth, removing the custom-fitted orthotic device from the user's mouth and chilling the orthotic device to below its moldable temperature, and detaching a spacer from each of two posterior regions of the orthotic device.

DETAILED DESCRIPTION OF THE INVENTION

Figure 1:
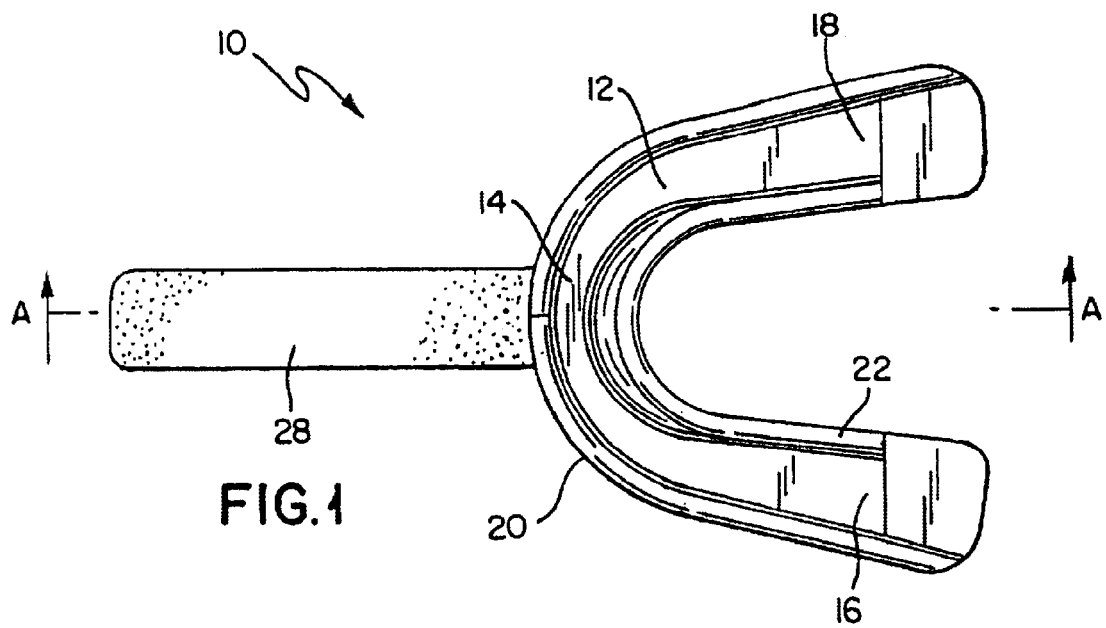
FIG. 1 is a top view of a first embodiment of the orthotic device.

Referring to FIG. 1, an orthotic device 10 according to one embodiment of the invention is shown. The orthotic device 10 includes a generally U-shaped tray 12, the tray 12 having an anterior region 14 and two posterior regions 16, 18. As shown most clearly in FIG. 2, the tray 12 further includes an outer wall 20 and an inner wall 22 that extend upwardly to form a channel 24 therebetween. The channel 24 is generally shaped to receive a user's upper teeth.

The tray 12 is formed from one or more thermoplastic materials which are moldable when heated. In one embodiment, the tray 12 is formed from an ethylene vinyl acetate copolymer resin having a melt index of 20 to 60 g/10 min. and a melting temperature ranging from about 35° C. to 80° C. This material has been selected in part for its low melting temperature so that a user can soften the tray 12 to a moldable state at home with hot water. Once the tray 12 has been heated to a moldable state, it can then be custom fit to the user's upper teeth in a fitting process herein described.

In other embodiments, the tray 12 is formed from at least two thermoplastic materials having different melting temperatures. When heated together to the same temperature, a softer grade thermoplastic material having a lower melting temperature becomes softer and more moldable than a firmer grade thermoplastic material having a higher melting temperature. Accordingly, by selectively locating different grade thermoplastic materials on the tray 12, it is possible to reduce the moldability of certain features on the tray 12 while retaining the moldability of certain other features. As one of ordinary skill in the art might contemplate, it may be desirable to utilize a firmer grade thermoplastic material on a bottom surface 26 of the tray 12 in order to retain the general U-shape of the tray 12 or to preserve the outer appearance of the tray 12. By contrast, it may be desirable to cover or fill the channel 24 with a softer grade thermoplastic material so that the tray can be molded to closely fit the user's upper teeth and gums. In one embodiment the channel 24 is filled with a thermoplastic material having a melt index of 35 to 70 g/10 min. and a melting temperature ranging from about 30° C. to 60° C. A strap 28 may be attached to the anterior region 14 of the tray 12 for handling the tray 12 during the fitting process. Specifically, the strap 28 allows a user to safely immerse the tray 12 in hot water and to handle the tray 12 without molding it while the tray 12 is still soft. The strap 28 can be attached to the tray 12 by any suitable means. For example, the strap 28 can be molded directly to the tray 12, or it can be attached using a pressure sensitive adhesive. After fitting the tray 12 to the user's upper teeth the strap 28 is detached from the tray 12 before use.

Figure 2:
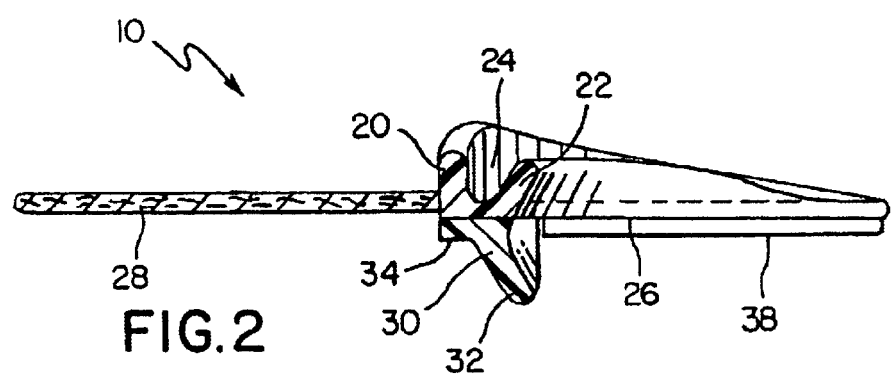
FIG. 2 is a cross-sectional side view of a first embodiment of the orthotic device taken along line A—A of FIG. 1.
Figure 3:
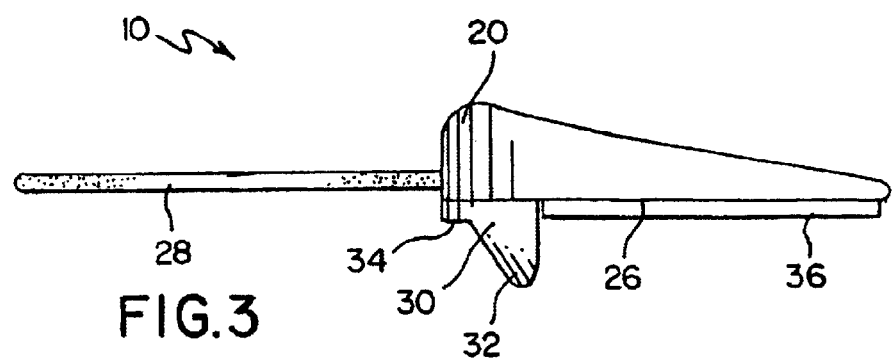
FIG. 3 is a side view of a first embodiment of the orthotic device.

Referring to FIGS. 2 and 3, a ramp portion 30 is attached to the bottom surface 26 of the anterior region 14 of the tray 12. In one embodiment, the ramp portion 30 is molded directly to the tray 12. In other embodiments, the ramp portion 30 may be attached to the tray 12 by other means including an adhesive.

The ramp portion 30 includes a guide ramp 32 that extends downwardly and posteriorly from the anterior region 14 of the tray 12. In one embodiment of the present invention the guide ramp 32 extends downwardly at an angle of about 45°. When the orthotic device 10 is worn by the user, the guide ramp 32 engages the lingual side of at least one of the user's lower anterior teeth in order to advance the user's lower jaw forward, thereby bringing the user's lower anterior teeth into substantial vertical alignment with the user's upper anterior teeth. Alternatively, the guide ramp 32 may be understood to simply rest lingually of the user's lower anterior teeth so as to prevent the user's lower jaw from retracting from the desired forward position. When the user's upper and lower anterior teeth are in substantial vertical alignment, the user's upper and lower posterior teeth cannot contact one another as is required for dental clenching.

The ramp portion 30 may also include a bite pad 34 that is located anteriorly with respect to the guide ramp 32. When the orthotic device 10 is worn by the user, the guide ramp 32 rests lingually of the user's lower anterior teeth and the bite pad 34 serves as a contact point for the tips of user's lower anterior teeth. In one embodiment of the present invention, the bite pad 34 may be approximately 2 to 3 millimeters thick so as to provide the correct spacing between the user's upper and lower anterior teeth to avoid tension in the jaw when the orthotic device 10 is worm. The total thickness of the bite pad 34 and the anterior region 14 of the tray 12 is not particularly limited but will typically be approximately 4 to 6 millimeters.

Like the tray 12, the ramp portion 30 is formed from a thermoplastic material so as to be moldable when heated. In accordance with particular embodiments of the present invention, the ramp portion 30 may be made from a firmer grade thermoplastic material than the tray 12. In one embodiment, the ramp portion 30 is formed from an ethylene vinyl acetate copolymer resin having a melt index of 15 to 50 g/10 min. and a melting temperature from about 45° C. to 90° C. This material was chosen in order to satisfy dual requirements. In particular, although the guide ramp 32 must be firm enough to retain its general shape when the orthotic device 10 is heated during the fitting process, the guide ramp 32 must also be soft enough when heated to allow the user to push the guide ramp 32 forward against the lingual side of the user's lower anterior teeth to conform to the shape of the user's mouth and the position of the tongue.

Thermoplastic materials useful in practicing the present invention are typically ethylene vinyl copolymer resins. Various grades of useful resins are commercially available under the trademark ELVAX®.

Figure 4:
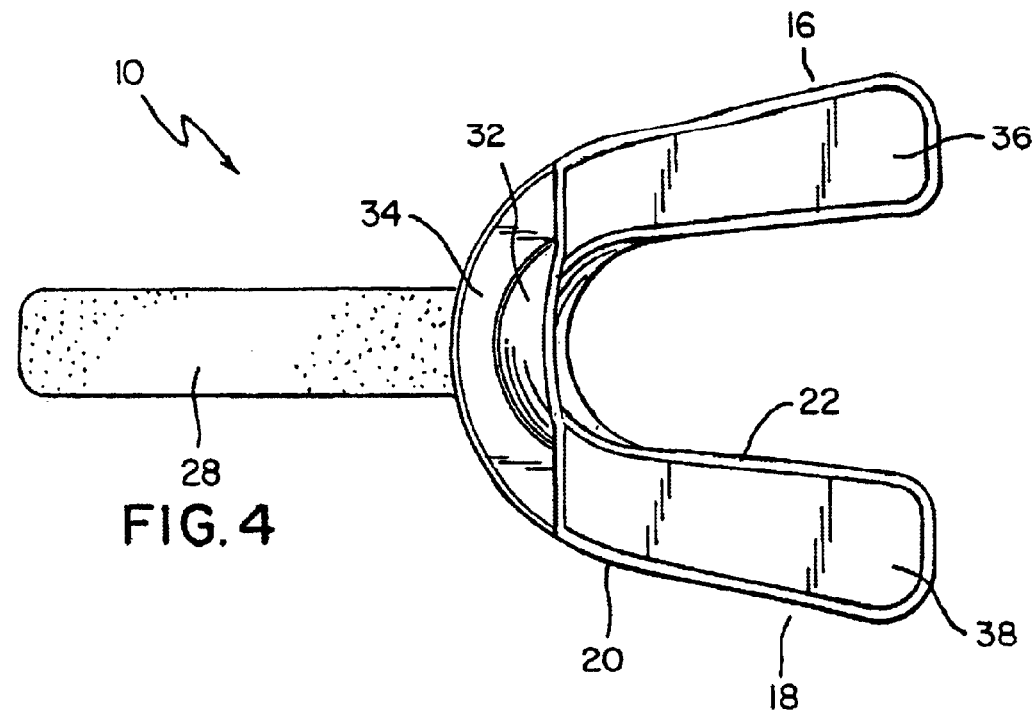
FIG. 4 is a bottom view of a first embodiment of the orthotic device.
Figure 5:
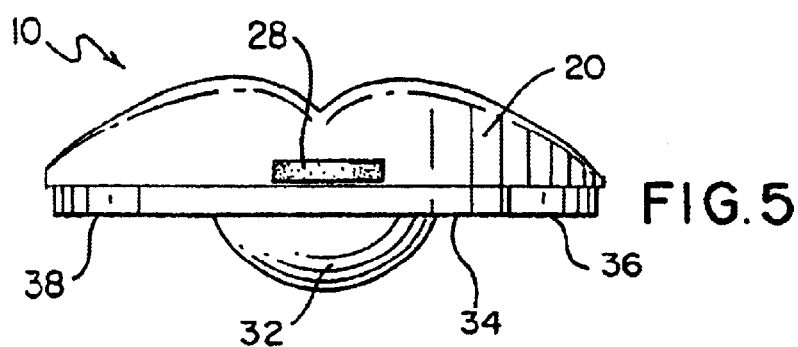
FIG. 5 is a front view of a first embodiment of the orthotic device.

Referring to FIGS. 2, 3, and 4, each posterior region 16, 18 of the tray 12 includes a bottom surface 26. Attached to each bottom surface 26 of the posterior regions 16, 18 is a spacer 36, 38 for providing a gap between the bottom surface 26 and the user's lower posterior teeth during the fitting process. In the embodiment that is shown, these spacers 36, 38 are flat pads which cover the entire posterior region 16, 18 of the tray 12 bilaterally. In accordance with one aspect of the invention, the spacers are fabricated from a vinyl acetate material. They may be attached to the tray by an adhesive, typically a pressure sensitive adhesive, or other suitable means.

Figure 6:
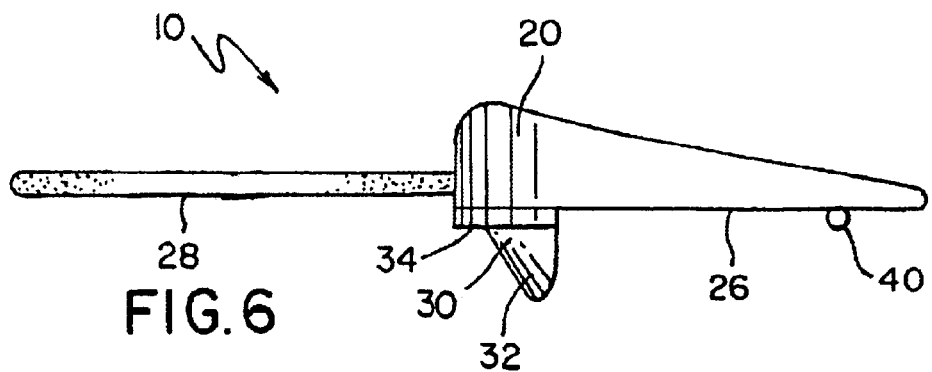
FIG. 6 is a side view of a second embodiment of the orthotic device having spherical bead spacers.

In another embodiment shown in FIG. 6, each spacer 40 is a spherical acrylic bead that can be attached to the tray 12 by a snap, a pressure sensitive adhesive, or other suitable means. After the fitting process, the spacers 36, 38 are detached from the tray 12 before use. Accordingly, when the fitted orthotic device 10 is worn, there is preferably no contact between the user's lower posterior teeth and the bottom surface 26 of the tray 12.

As previously stated, the orthotic device 10 of the present invention operates by advancing the user's lower jaw forward, thereby bringing the user's lower anterior teeth into substantial vertical alignment with the user's upper anterior teeth. When the user's anterior teeth are in substantial vertical alignment, the user's upper and lower posterior teeth cannot contact one another as is required for dental clenching. If, after the fitting process, the posterior regions 16, 18 of the tray 12 are in contact with the user's lower posterior teeth, then dental clenching may nevertheless occur as a result of indirect engagement of the user's upper and lower posterior teeth through the tray 12. Accordingly, in order for the orthotic device 10 to function correctly, the posterior regions 16, 18 of the tray 12 must not contact the user's lower posterior teeth after the fitting process.

In a second aspect of the present invention, a method of custom fitting the orthotic device 10 is provided. The first step of the fitting process involves heating the orthotic device 10 to a temperature at which it becomes moldable. Heating is accomplished by immersing the orthotic device 10 in hot, post-boiled water at approximately 190° F. Once the orthotic device 10 has been softened through heating, it is inserted into the user's mouth such that the user's upper teeth are received in the channel 24 of orthotic device 10 and such that the guide ramp 32 is directed downwardly and posteriorly into the user's mouth. To ensure that the orthotic device 10 fits snuggly to the user's upper teeth and gums, the user may use finger pressure to push the softened orthotic device 10 around the user's upper teeth.

In addition to fitting the tray 12 to the user's upper teeth, the guide ramp 32 must also be customized to ensure that the user's lower jaw is properly positioned during use. Accordingly, the fitting process includes the steps of posturing the user's lower jaw forward and bringing the user's lower anterior teeth into substantial vertical alignment with the user's upper anterior teeth. Once the user's jaw and teeth are properly positioned, the partially moldable guide ramp 32 is then pushed forward against the lingual side of the user's lower anterior teeth using the tongue.

After maintaining the orthotic device 10 in the proper position for approximately three minutes, the custom-fitted orthotic device 10 is then removed from the user's mouth and cooled below its moldable temperature. Cooling may be accomplished by allowing the orthotic to return to ambient temperature or by immersing the orthotic device in cold water. If, after performing the preceding steps, the orthotic device 10 does not fit properly, the fitting process may be repeated. Before use, the strap 28 attached to the anterior region ~14 of the tray 12 and the spacers 36, 38 attached to the bottom surface 26 of the posterior regions 16, 18 of the tray 12 are removed.

What is claimed is:

1. An orthotic device for reducing dental clenching comprising:
   a generally U-shaped tray having an outer wall and an inner wall, wherein the outer wall and the inner wall extend upwardly forming a channel therebetween for receiving a user's upper teeth, the tray further having an anterior region and two posterior regions, wherein each posterior region includes a bottom surface, the bottom surface having a spacer releasably attached thereto for providing a gap between the bottom surface of the posterior region and the user's lower posterior teeth during fitting of the orthotic device; and
   a ramp portion attached to the tray, the ramp portion including a guide ramp extending downwardly and posteriorly from the anterior region of the tray for engaging at least one of the user's lower anterior teeth thereby advancing the user's lower jaw to bring the lower anterior teeth into substantial vertical alignment with the user's upper anterior teeth.

2. The orthotic device of claim 1 wherein the tray and ramp portions are composed of a thermoplastic ethylene vinyl acetate copolymer resin.

3. The orthotic device of claim 2 wherein said ethylene vinyl acetate copolymer resin has a melt index of 15 to 60 g/10 min. and a melting temperature from about 35° C. to about 90° C.

4. The orthotic device of claim 1 wherein said tray and ramp portion are each composed of a thermoplastic ethylene vinyl acetate copolymer resin, the respective thermoplastic ethylene vinyl acetate copolymer resins having differing melt indexes and melting temperatures.

5. The orthotic device of claim 4 wherein said tray is composed of at least one ethylene vinyl acetate copolymer resin having a melt index of 20 to 60 g/10 min. and a melting temperature from about 35° C. to about 80° C. and said ramp portion is composed of at least one ethylene vinyl acetate copolymer resin having a melt index of 15 to 50 g/10 min. and a melting temperature from about 45° C. to about 90° C.

6. The orthotic device of claim 4 wherein the channel is partially filled with a thermoplastic resin having a melt index of 35 to 70 g/10 min. and a melting temperature from about 30° C. to about 60° C.

7. The orthotic device of claim 1 wherein said ramp portion is molded directly to said tray.

8. The orthotic device of claim 1 wherein said ramp portion is attached to said tray with an adhesive.

9. The orthotic device of claim 1 wherein said guide ramp extends downwardly at an angle of about 45°.

10. The orthotic device of claim 1 wherein said spacer is releasably attached to the bottom surface of the posterior region with a pressure sensitive adhesive.

11. The orthotic device of claim 1 wherein said spacer is a flat pad.

12. The orthotic device of claim 11 wherein said spacer is fabricated from a vinyl acetate.

13. The orthotic device of claim 1 wherein said spacer is a spherical bead made from an acrylic resin.

14. The orthotic device of claim 1 further comprising a strap attached to the anterior region of said tray wherein said strap is used as a handle during the fitting process.

15. The orthotic device of claim 1 wherein the ramp portion further includes a bite pad for engaging the user's lower anterior teeth when the orthotic device is worn.

16. A method of custom fitting the orthotic device of claim 1 comprising the steps of:
   a. heating the orthotic device to a temperature at which the tray and ramp portion become moldable; and
   b. fitting the orthotic device around the user's upper teeth with said guide ramp directed posteriorly into the mouth.

17. The method of claim 16 wherein said fitting step comprises the steps of:
   inserting the orthotic device in the user's mouth such that the user's upper teeth are received in said channel with said guide ramp directed posteriorly into the mouth;
   posturing the user's lower jaw forward and bringing the lower anterior teeth into substantial vertical alignment with the upper anterior teeth; and
   pushing the moldable guide ramp forward against the lingual of the lower anterior teeth.

18. The method of claim 16 further comprising the steps of:
   c. cooling the orthotic device to below its moldable temperature; and
   d. removing the spacers.

19. The method of claim 16 wherein said heating step comprises the steps of boiling a quantity of water, allowing the water to cool to a temperature of approximately 185° F. to 195° F., and immersing the orthotic device in the water until said tray and ramp portion are moldable.

* * * * *